United States Patent
Löfgren et al.

(10) Patent No.: US 10,145,813 B2
(45) Date of Patent: Dec. 4, 2018

(54) URINE PRODUCTION HANDLING DEVICE AND METHOD

(71) Applicant: Observe Medical ApS, Lyngby (DK)

(72) Inventors: Mikael Löfgren, Mölndal (SE); Mikael Charlez, Mölndal (SE)

(73) Assignee: OBSERVE MEDICAL APS, Kongens Lyngby (DK)

( * ) Notice: Subject to any disclaimer, the term of this patent is extended or adjusted under 35 U.S.C. 154(b) by 932 days.

(21) Appl. No.: 14/358,610

(22) PCT Filed: Nov. 15, 2012

(86) PCT No.: PCT/EP2012/072771
§ 371 (c)(1),
(2) Date: May 15, 2014

(87) PCT Pub. No.: WO2013/072430
PCT Pub. Date: May 23, 2013

(65) Prior Publication Data
US 2014/0327453 A1  Nov. 6, 2014

(30) Foreign Application Priority Data

Nov. 16, 2011 (SE) ..................................... 1151089

(51) Int. Cl.
| | |
|---|---|
| *G01F 3/38* | (2006.01) |
| *G01N 27/24* | (2006.01) |
| *A61B 5/20* | (2006.01) |
| *G01F 25/00* | (2006.01) |
| *G01F 23/26* | (2006.01) |

(52) U.S. Cl.
CPC ............. *G01N 27/24* (2013.01); *A61B 5/208* (2013.01); *G01F 3/38* (2013.01); *G01F 23/263* (2013.01); *G01F 25/0061* (2013.01); *A61B 2560/0223* (2013.01)

(58) Field of Classification Search
CPC ....................................................... G01N 27/24
USPC ............... 324/679, 658, 649, 600, 439, 601; 435/34; 73/304 C
See application file for complete search history.

(56) References Cited

U.S. PATENT DOCUMENTS

| | | | |
|---|---|---|---|
| 3,919,455 A | 11/1975 | Sigdell et al. | |
| 5,283,034 A * | 2/1994 | Okrongly | ............... A61K 35/12 422/20 |

(Continued)

FOREIGN PATENT DOCUMENTS

| | | |
|---|---|---|
| CN | 101308158 A | 11/2008 |
| CN | 101490567 A | 7/2009 |

(Continued)

*Primary Examiner* — Benjamin Klein
*Assistant Examiner* — Sara Sass
(74) *Attorney, Agent, or Firm* — RMCK Law Group, PLC

(57) ABSTRACT

Method for automatically, with the aid of a processor, determining a surface degeneration of a first surface of a urine handling system, the first surface being intended to come into contact with urine, the method comprises the following main steps: a) repeatedly measuring one or more capacitive values of the first surface, forming capacitive measurements; b) storing all, or representative instants of the capacitive measurements; c) deciding, based on changes of the stored capacitive measurements, that a significant surface degeneration of the first surface has occurred.

10 Claims, 14 Drawing Sheets

(56) References Cited

U.S. PATENT DOCUMENTS

| | | | |
|---|---|---|---|
| 8,233,957 B2* | 7/2012 | Merz | A61B 5/053 600/345 |
| 2003/0108823 A1* | 6/2003 | Muraoka | B08B 3/02 430/329 |
| 2004/0178804 A1 | 9/2004 | Allen et al. | |
| 2008/0286158 A1 | 11/2008 | Watanabe et al. | |
| 2009/0047256 A1* | 2/2009 | Bettinger | A61L 27/18 514/1.1 |
| 2009/0197243 A1* | 8/2009 | Rieder | C12Q 1/02 435/5 |
| 2010/0094173 A1* | 4/2010 | Denton | A61M 1/0043 600/584 |
| 2010/0262375 A1* | 10/2010 | Shachar | G01N 33/54373 702/19 |
| 2011/0314907 A1 | 12/2011 | Wiedekind-Klein | |

FOREIGN PATENT DOCUMENTS

| | | |
|---|---|---|
| EP | 2 400 275 A1 | 12/2011 |
| JP | 2010121962 A | 6/2010 |
| WO | WO-2008042003 A2 | 4/2008 |
| WO | 2010149708 A1 | 12/2010 |

\* cited by examiner

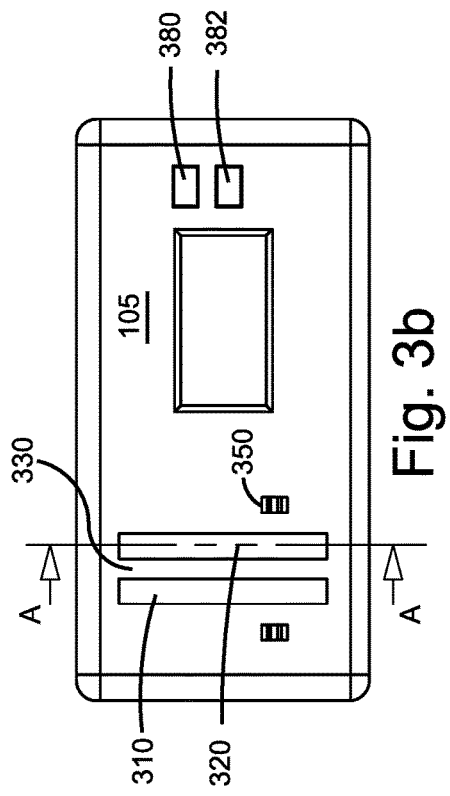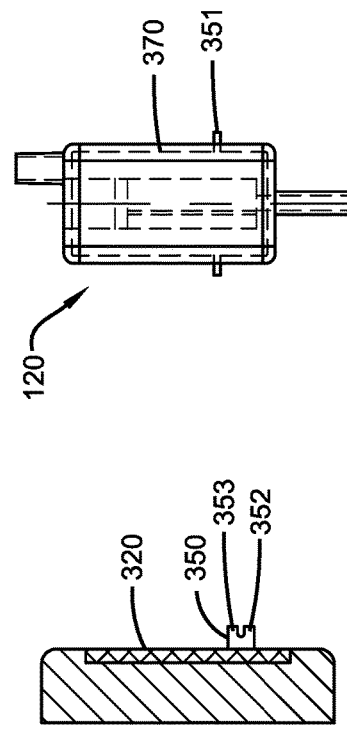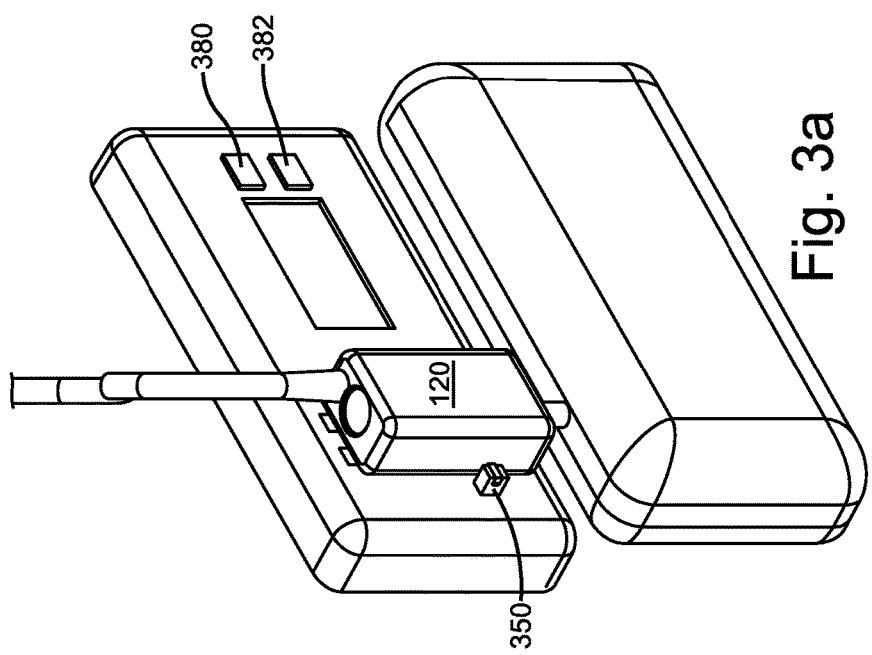

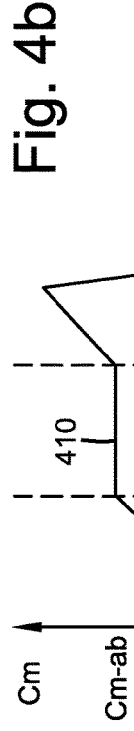
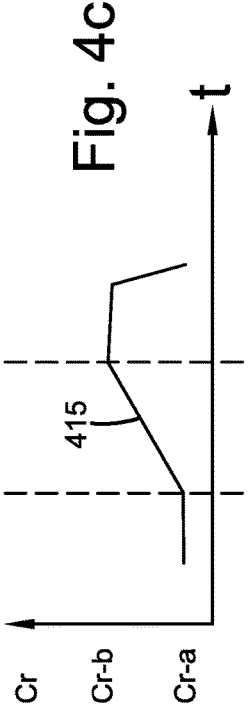
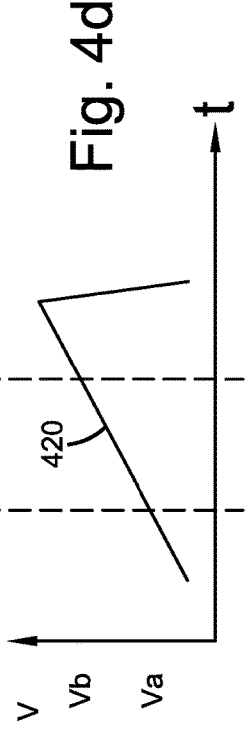
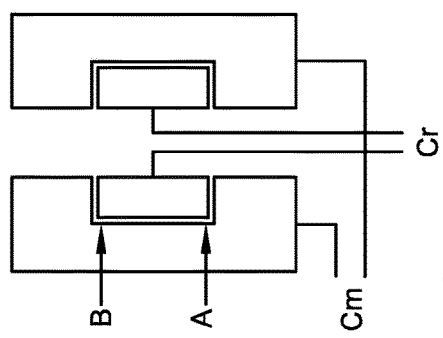

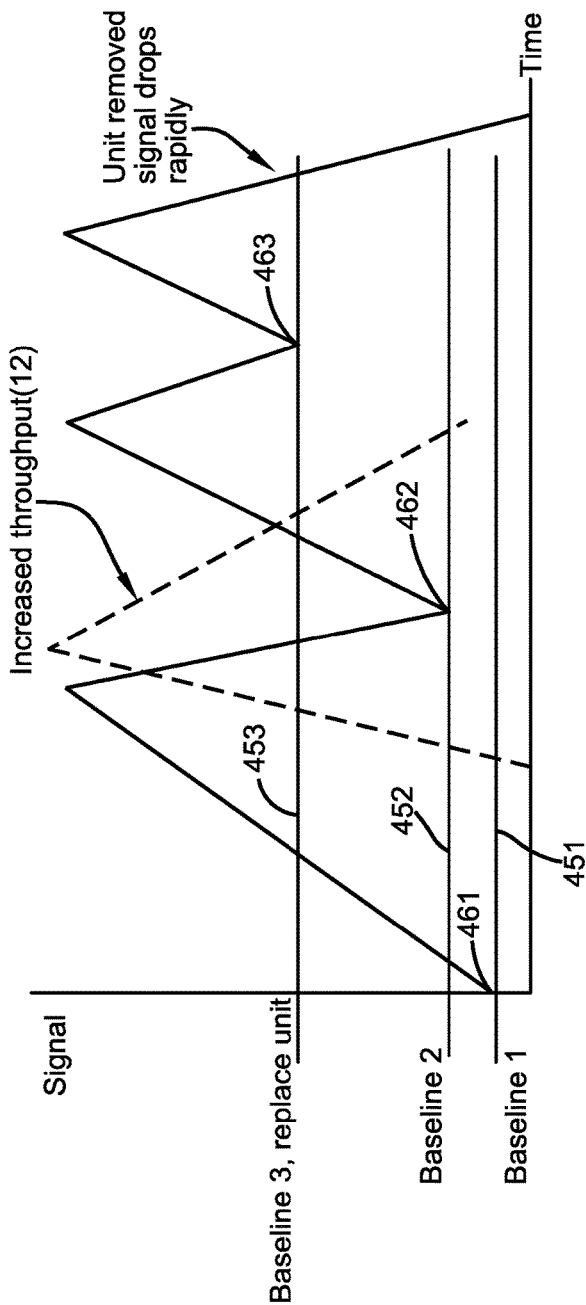

URINE PRODUCTION HANDLING DEVICE AND METHOD

REFERENCE TO RELATED APPLICATIONS

The present application is a National Stage of PCT International Patent Application No. PCT/EP2012/072771, filed Nov. 15, 2012, which claims the benefit of Swedish Patent Application No. 1151089-8, filed Nov. 16, 2011, whose disclosures are hereby incorporated by reference in their entireties into the present disclosure.

TECHNICAL FIELD

The present invention relates to a device and a method for improved electronic urine measurements. More specifically it relates to sensor arrangement, signal processing, and signal interpretation methods of signals coming from a capacitive sensor system of a urine handling system for handling the urine production of a patient having a urine catheter.

BACKGROUND ART

Electronic urine measurement systems are known.

WO 2010/149708 A1 discloses a urine measurement device for measuring urine production of a patient having a urine catheter. The device uses capacitive measurements from electrodes arranged close to a self emptying measurement chamber to calculate the urine level in the measurement chamber.

U.S. Pat. No. 3,919,455 describes a device comprising a siphon chamber for the urine with a self emptying function, and wherein the urine volume is measured with the aid of an optic and/or electric sensor. When the urine level in the siphon chamber increases the capacitance between two electrodes in the walls of the siphon chamber changes. In this way a signal is created that corresponds to the amount of urine in the siphon chamber. See e.g. FIG. 4 and column 4 lines 34 to 52.

More details regarding nosocomial urinary tract infections and development of biofilms may be found in Burke J P, Riley D K. *Nosocomial urinary tract infection*. In: Mayhall C G, editor. Hospital epidemiology and infection control. Baltimore: Williams and Wilkins; 1996. p. 139-53.

D. J Stickler, S. D Morgan, *Observations on the development of the crystalline bacterial biofilms that encrust and block Foley catheters*, Cardiff School of bioscience 2007

SUMMARY OF THE INVENTION

A significant percentage of nosocomial bladder infections among patients are intraluminal due to contamination of a closed urinary drainage system used to treat the patient. This occurs by reflux (retrograde contamination) of microorganisms gaining access to a drainage system catheter lumen and the urinary bladder. Over time the intraluminal surface of the closed system (catheter, other tubing, measurement chamber and collection bag) will be degraded by the formation of biofilm containing the infecting microorganisms embedded in a matrix of host proteins and microbial exoglycocalyx. Bacteria use this biofilm to reach the patient's urine bladder. The biofilm formation rate is very individual and a urine measurement system according to the invention will detect when the inner surface becomes degraded to a critical level and alert the user to replace the disposable part.

Urine meter systems in general are depending on a connection to a urine catheter in order to get access to the urine-bladder and drain urine from the bladder through a tubing system via a measuring unit and then collect the urinary output into a collection bag. Urinary Tract Infection (UTI) is the most common nosocomial infection within the healthcare system today. The UTI extends length of stay, increase costs and contributes to an additional risk to the patients' health status. It's usually related to the installation of said urine catheter. It's revealed through clinical research that the risk of UTI increases by 10% each day the catheter stays in the urinary tract. Bacteria has either their entrance from the outside of the body (64%) or from the very inside (36%).

It has been understood through literature studies that in in-vitro system bacterial colonisation generates a bio film that becomes mineralised (encrustation). In sterile urine, the development of encrustation has been shown to be dependent on urinary properties such as pH and ionic strength as well as on the biomaterial hydrophobic properties. Urine is generally free from bacteria and thus it is the chemistry of the urine in a measuring and/or collecting environment that dominates the variables. In infected urine, enzyme urease produced by adhered bacteria hydrolyses the urea to produce ammonia. This elevates the urine pH, a condition that favours the precipitation of magnesium and calcium in the form of struvite and hydroxyapatite (HA). These minerals are two major component of encrustation.

Said bio-film formation and related risk of nosocomial UTIs are initially not visible to the human naked eye. The present invention, providing a signal processing method, may reveal an early stage of bio-film formation before it leads to excessive bacteria growth and related pH elevation, that may nurture further bacteria growth. A urine measurement system according to the present invention overcomes said problem of detecting a non visible bio-film formation and may subsequently alert the care giving personnel to replace a degenerated disposable part of the system.

Thus a urine measurement system according to the present invention comprises a measurement chamber, subjected to urine flow. The chamber may be of a self emptying siphoning type, that is, the chamber, when it becomes full, empties itself by means of siphoning technique. A problem that may arise is that the measurement chamber may within unforeseeable time suffer from a surface degeneration on its inside surface caused by forming of a non-macroscopic bio-film due to aggressive urine properties, see also above. In this context "non-macroscopic" should be interpreted as "invisible to the naked eye". Surface degeneration may cause measurement errors of a capacitive sensor system devised to measure the amount of urine produced, and may also cause dysfunctional emptying procedures of the self emptying siphoning measurement chamber. The present invention manages said surface degeneration and is also capable of handling inappropriate use by providing the measurement system with an intelligent signal processing method.

The Problem

Urine is a body liquid that may be very aggressive on manmade surfaces, in particular on surfaces inside a urine measurement system. The urine measurement system according to the invention is a closed system that comprises a tubing system connected to a patient's catheter, a measurement chamber and a collection bag. The tubing system leads the urine from the urine bladder to the measurement chamber where a capacitive, contact-less sensor system senses the signals through the wall of the measurement chamber, and thereof calculates the volume. The chamber wall is of a rigid polymeric material, but may be of another suitable material, e.g. glass. The urine is collected in a collection bag after it has been measured. Such a collection bag may be of a flexible polymeric material, and have a volume considerably larger than the volume of the measurement chamber.

The measurement chamber may be a self-emptying type of chamber and it is devised to empty at a certain volume (15-20 ml). The challenge in said self-emptying measurement chamber is to handle the effects of a degenerative process compromising the electric and physical properties of the delicate surfaces of the measurement chamber caused by the urine over time.

Thus, the inventor has realised that within an unforeseeable amount of time there is a decrease of signal through the measurement chamber wall that must be caused by a bio film formation on the surface(s) corresponding to where the sensors are arranged. There may also arise a degeneration of the delicate surface within the region of the self-emptying system which may lead to a dysfunction of the self-emptying mechanism.

The unpredictable lifetime of the measurement chamber is very individual and may be further reduced if the patient suffers from urine infection, or if there is existence of Ph elevation due to urine decomposition, pharmaceutical drugs, diabetes, inappropriate food intake, or disturbed metabolism (acidosis, alkalosis).

Said urine measurement system with a certain emptying volume may also be subject to emptying prior to the level where the predetermined volume is achieved.

Said system may also be subjected to a rapid flush of urine (milking) through the measurement chamber and, as a consequence, the sensor system might not be able to measure the incoming volume during the emptying procedure. Milking is usually caused by misdirected action of care personnel.

The measurement chamber may be disposable and interchangeable.

The Solution

The solution to the described challenges of the measurement system is to put more intelligence into the interpretation of signals from the sensor system. If the signals are analysed and then interpreted in the meaning of whether they are correct or incorrect would reveal when there is a non-macroscopic degeneration of the delicate surface that within shortly may cause a significant accuracy deviation on measured urine volume. A signal processing unit adapted according to the invention may alert the user to change the disposable measurement unit and mount a new one prior to malfunction of both signal transfer and self-emptying mechanism.

If the system begins to execute premature emptying sequences, it is likely that surface(s) of the measurement chamber critical to initiation of the self-emptying sequence, have/has become compromised. The solution according to the invention to avoid these premature emptying procedures and disturbed volume measurements is to arrange a reference sensor in a clever way, in this case in the middle of the sensor system which may serve as an offset point or checkpoint. Further, the solution includes a signal processing method comprising several steps. The offset point or checkpoint may serve as a self-calibration sensor and provide sensor values that can be used by a self-calibration function to successfully perform a self-calibration, that is to establish what sensor values that corresponds to certain urine levels in the measurement chamber. In this way also a half-full chamber could be correctly added to the measurement record after the emptying procedure.

The measurement chamber may also be subjected to a flush of urine during the filling or emptying procedure. When this happens, the signal becomes respectively steeper or more extended than normal. The processing unit is provided with means for calculating the angle of the sensor curve, i.e., the so called slope of the sensor curve, during filling and emptying.

To compensate for flush of urine a constant may be added to the expected volume to represent the true value (expected volume+constant=true volume).

Thus, according to a first aspect of the invention, there is provided a urine measurement device for measuring the production of urine of a patient wearing a urine catheter, wherein the device comprises a self-emptying measurement chamber (120) to which urine from the patient is conveyed via the catheter, the device is also provided with a set of electrodes (620) arranged to sense a changing capacitance (Cm(t)) corresponding to changing levels of urine in the self-emptying measurement chamber (120), wherein the set of electrodes comprises:

a first electrode (140, 310, 652)
a second electrode (320, 654)

between which the changing capacitance (x, Cm(t)) is measured, and wherein the device further comprises a socket (350, 136, 137, 138, 139, 660) for the self emptying measurement chamber (120), and wherein the self emptying measurement chamber (120) is replaceable and wherein the first and second electrodes (140, 310, 652, 320, 654) to sense the changing capacitance corresponding to changing levels of urine in the measurement chamber (120) are arranged at the socket wall (137, 139, 330) to face the measurement chamber (120), the device further comprises a data processing unit (610) connected to the electrodes (140, 310, 652, 320, 654) to keep track of produced urine volume and a baseline level tracker (650) arranged to determine and keep track of a varying baseline level, i.e., a capacitance value corresponding to an empty self-emptying measurement chamber, based on the changing capacitance, as multiple self-emptyings of the self-emptying measurement chamber ensue.

According to a second aspect of the invention there is provided a urine measurement device for measuring the production of urine of a patient wearing a urine catheter, wherein the device comprises a self-emptying measurement chamber (120) to which urine from the patient is conveyed via the catheter, the device is also provided with a set of electrodes (620) arranged to sense a changing capacitance (Cm(t)) corresponding to changing levels of urine in the self-emptying measurement chamber (120), wherein the set of electrodes comprises:

a first electrode (140, 310, 652)
a second electrode (320, 654)

between which the changing capacitance (x, Cm(t)) is measured, and wherein the device further comprises a socket (660, 350, 136, 137, 138, 139) for the self emptying measurement chamber (120), and wherein the self emptying measurement chamber is replaceable and wherein the first and second electrodes to sense the changing capacitance corresponding to changing levels of urine in the measurement chamber are arranged at the socket wall to face the measurement chamber, and wherein the urine measurement device further comprises a reference sensor (655) arranged to detect and determine a first point in time when the urine level in the measurement chamber reaches a known predetermined level corresponding to a known volume, the device further comprises a data processing unit (610) connected to the electrodes (140, 310, 652, 320, 654) and arranged to keep track of produced urine volume, and a self calibration unit (657) arranged to determine and keep track of one or more self-calibration parameters, i.e., parameters that may be used to improve estimations of urine volume calculated from a measured capacitance value, based on the determined first point in time, the predetermined known volume, and the changing capacitance, as multiple self-emptyings of the self-emptying measurement chamber ensue.

Further, the device according to directly above may further comprise a baseline level tracker (650) to determine and keep track of a varying baseline level (451, 452, 453), i.e., a capacitance value corresponding to an empty self-emptying measurement chamber (120), based on the determined first point in time, the known volume, and the changing capacitance, as multiple self-emptyings of the self-emptying measurement chamber ensue.

The device according to above may comprise an alarm unit (662) capable of issuing an alarm when the baseline level reaches a predetermined threshold value.

The device according to above wherein the determinations of baseline level and/or self-calibration parameters are also based on the detection of start of self emptying events i.e., abrupt plummet of measured capacitance value The device according to above wherein the determinations of baseline level and/or self-calibration parameters are also, or alternatively based on the detection of endpoint (462, 463) of self emptying events i.e., abrupt ceasing of plummeting measured capacitance value.

According to a third aspect of the invention there is provided a urine measurement device for measuring the production of urine of a patient wearing a urine catheter, wherein the device comprises a measurement chamber to which urine from the patient is conveyed via the catheter, the device is also provided with a set of electrodes arranged to sense the changing capacitance corresponding to changing levels of urine in the measurement chamber, wherein the set of electrodes comprises:

a first electrode (E1) having a first portion (E1a) and a second portion (E1b);

a second electrode (E2) having a first portion (E2a) and a second portion (E2b)

wherein the first portion and the second portion respectively, are arranged apart a first and a second distance respectively, in the direction of increasing urine level in the measurement chamber, and are also connected to each other by a conducting material, the set of electrodes further comprises a third electrode (E3);

a fourth electrode (E4);

wherein the first and second electrodes are arranged parallel to each other and with a length axis parallel to the direction of increasing urine level, and;

wherein the third electrode (E3) is arranged having a major portion between the first portion (E1a) and the second portion (E1b) of the first electrode in the direction of increasing urine level, and;

wherein the fourth electrode (E4) is arranged having a major portion between the first portion (E1a) and the second portion (E1b) of the first electrode in the direction of increasing urine level, and;

wherein a processing unit (610) is connected to the first, second, third, and fourth electrodes (E1, E2, E3, E4) and arranged to interpret changes in capacitance levels between the electrodes as corresponding to different levels of urine, and also corresponding to different physiochemical conditions inside the measurement chamber.

The urine measurement device according to above wherein the measurement chamber is of a self-emptying siphoning type.

The urine measurement device according to above wherein the measurement chamber is easy replaceable in a recess or docking site of the urine measurement device, and the electrodes are arranged at the walls of the recess or docking site such that they touch snugly towards a measurement chamber placed in the recess or docking site.

According to a fourth aspect of the invention there is provided a method for detecting a compromised measurement chamber during measurement of urine production using a urine measuring device comprising:

a replaceable measurement chamber to which urine from a patient is conveyed via a catheter to fill the measurement chamber, a set of electrodes, comprising at least two electrodes, connected to a processor, and arranged to sense the changing capacitance corresponding to changing levels of urine in the replaceable measurement chamber, emptying means to empty the measurement chamber when full, a level sensor for indication when urine level has reached a known position of the measurement chamber;

the method comprising the following steps:

Measuring and/or deriving a sensed capacitance value (x, Cm(t)) corresponding to a capacitance between first two electrodes of the set of electrodes Determining an original baseline level equal to a sensed capacitance value corresponding to an empty measurement chamber;

Detecting emptying events of the measurement chamber;

Measuring the capacitance corresponding to finished emptying events to measure new baseline level Keeping track of changing baseline level as multiple emptying events ensue;

The method according to above further comprising the step of:

issuing an alarm when the baseline level has reached a predetermined threshold

The method according to above wherein the detecting of emptying events is based on detection of endpoint of self emptying events i.e., abrupt ceasing of a plummeting measured capacitance value.

According to a fifth aspect of the invention there is provided a method for measuring urine production using a urine measuring device comprising a measurement chamber to which urine from the patient is conveyed via a catheter to fill the measurement chamber, a set of electrodes, comprising at least two electrodes, connected to a processor, and arranged to sense the changing capacitance corresponding to changing levels of urine in the measurement chamber, emptying means to empty the measurement chamber when full, a level sensor for indication when urine level has reached a know position;

the method comprising the following steps:

A—Measuring and/or deriving a first capacitance value (x, Cm(t)) corresponding to a capacitance between first two electrodes of the set of electrodes B—Defining a reference points corresponding to a known urine volume in the measurement chamber;

C—Providing a sensor that indicates when the known urine volume is reached
D—Using the information gathered in the above steps to effectively calibrate a volume calculating function, during each filling-emptying cycle,
E—Calculating an estimated urine volume using the calibrated volume calculating function.

The method according to above wherein a volume estimation function is provided of the type $$y=kx+m$$

wherein y is the estimated volume, k is a first calibration parameter, x is a measured and/or derived capacitance value, and m is a second calibration parameter, and
wherein the volume estimation function is used to estimate the urine volume production, and
wherein the calibration parameters k and m are determined by solving, with the aid of the processor, the equation y=kx+m for at least two known values of y, during the normal operation of the urine measurement system of the method.

According to a sixth aspect of the invention there is provided a method for measuring urine production using a urine measuring device comprising a measurement chamber to which urine from the patient is conveyed via a catheter to fill the measurement chamber, the device also being provided with a set of electrodes connected to a signal processing unit, and arranged to sense the changing capacitance corresponding to changing levels of urine in the measurement chamber, the device also being provided with emptying means to empty the measurement chamber when full, the method comprising the following steps:
a—Measuring a main capacitance Cm(t) between first two electrodes of the set of electrodes
b—Measuring a reference capacitance Cr(t) between second two electrodes of the set of electrodes;
c—Defining reference points corresponding to actual physical boundaries of the first and/or second electrodes (which the urine level surface will pass by during filling and emptying;
d—Using the curves of Cm(t) and Cr(t) to identify the capacitance(s) corresponding to actual physical boundaries of the first and/or second electrodes;
e—Using the information gathered in the above steps to effectively calibrating the sensors during each filling-emptying cycle, and to display as accurate volume readings as possible.

The method according to above further comprising the following step(s):
Determining the measurement chamber current volume Vsip to be a function of main capacitance Cm(t), reference capacitance Cr(t) and calibration parameters corresponding to capacitances measured when urine level is equal to an upper or lower end of an electrode The method according to above further comprising the steps of:
Determining a value of the highest momentary volume Vtop during a filling-emptying cycle to maximum of the volume in the measurement chamber Vsip and former highest momentary volume Vtop;
Determining the volume produced this hour, Vth, to be the sum of present sum of emptying volumes during present hour, Vth_bag, and the volume of the urine in the measurement chamber, Vsip;
Deciding if derivative dV/dt is less than flush constant Kflush, and if so setting the sum of emptying volumes during present hour Vth_bag to the sum of highest momentary volume Vtop and inflowing volume during emptying Vin_while_flush and setting highest momentary volume Vtop subsequently to 0;

The method according to above further comprising the step(s) of:
Deciding if a new hour has started, and if so setting total accumulated urine volume Vacc to the sum of total accumulated urine volume Vacc and volume produced this hour Vth, and setting volume produced previous hour Vph to volume produced this hour Vth, and setting the sum of emptying volumes during present hour Vth_bag to minus the volume in the measurement chamber Vsip
Setting volume produced this hour, Vth to zero

BRIEF DESCRIPTION OF THE DRAWINGS

The invention will now be further explained with the aid of one or more embodiments of the invention in conjunction with the accompanying drawings of which:
FIGS. 1c and 1d shows in more detail a base station part of the device of FIG. 1a.
FIG. 3a shows a urine measuring device wherein a burette is attached to a base unit having capacitance electrodes arranged on a flat surface.
FIG. 3b shows a base unit of the device of FIG. 3a, with the burette removed.
FIG. 3c shows the base unit of FIG. 3b in cross section.
FIG. 3d shows a burette of the device of FIG. 3a, detached from the base unit.
FIG. 4a shows an electrode arrangement together with certain reference.
FIG. 4b shows a capacitance curve for main capacitance as a function of time.
FIG. 4c shows a curve for reference capacitance as a function of time.
FIG. 4d shows a curve for chamber measurement volume as a function of time.
FIG. 4f shows a simplified capacitance curve of a urine measurement system exhibiting baseline alteration.

DETAILED DESCRIPTION

Figure 1A:
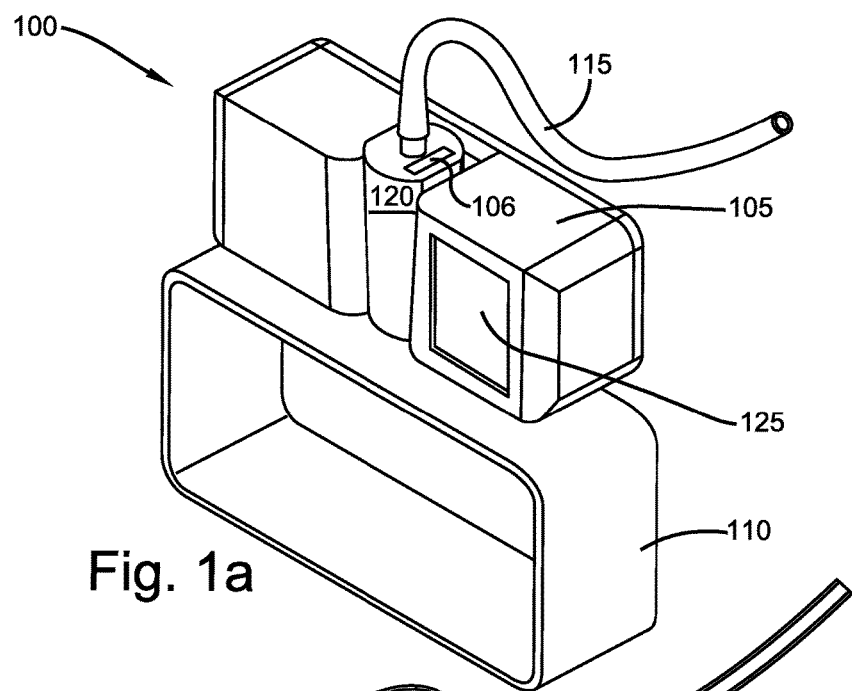
FIG. 1a shows a perspective view of urine measuring device for measuring of urine production.
Figure 1B:
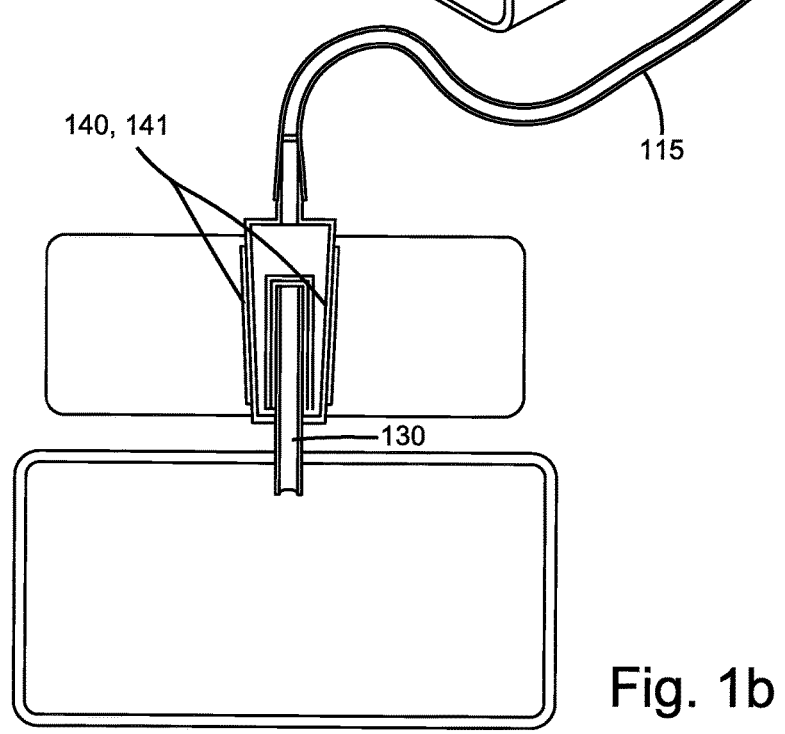
FIG. 1b shows the device of FIG. 1a in a planar cross section.
Figure 1C:
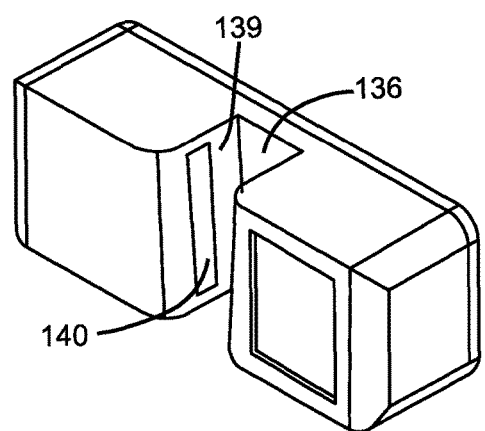
Figure 1D:
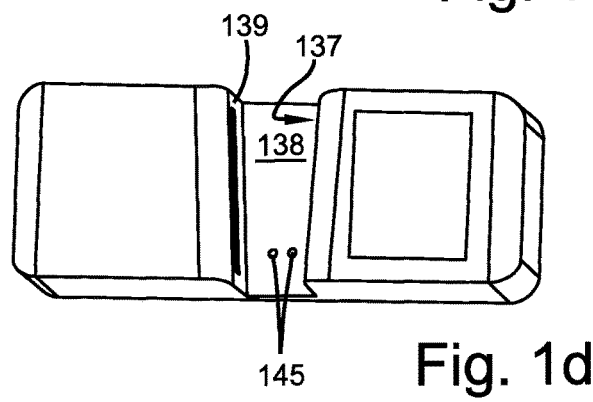
Figure 1E:
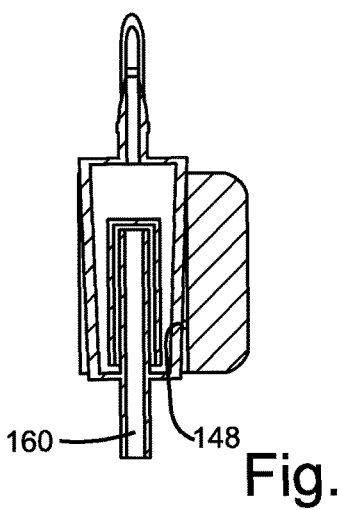
FIG. 1e shows, in cross section, a siphon measurement chamber (burette) arranged in a cavern of the base station.
Figure 1F:
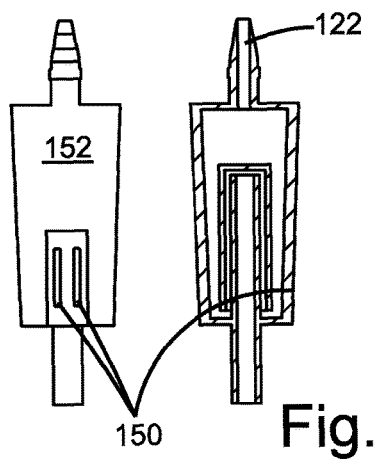
FIG. 1f shows the burette from the behind and in cross section.

FIG. 1a to 1f shows a urine measuring device 100 for measuring of urine production of a patient carrying a urine catheter, the device comprising a measurement vessel, or chamber 120, also called burette, provided with a siphon for self emptying when the burette 120 becomes filled up to a predetermined volume. The burette 120 further comprises an inlet 122 and an outlet 130, 160 for the urine whose volume is to be measured. Further, the device comprises a base station 105 provided with a cavern 138 for placing the burette 120 into, the side walls of the cavern 138 having left 139, right 137 and back 136 side walls, and being provided with two capacitance electrodes 140, 141 placed apart relative to each other, and capable of sensing a capacitance signal occurring between the two capacitance electrodes. The burette 120 is provided with a ventilation opening 106 to allow air to escape the burette when urine enters. The capacitance signal changes as the level of urine in the burette 120 changes, and the capacitance signal constitutes a measure of the produced amount of urine. A processor 610 is arranged to, with the aid of signal processing of the capacitance signal, keep record of how many times the burette has been emptied, and to continuously monitor the urine volume production between emptying procedures. The processor is configured to calculate the urine production as a function of time. The processor is preferably arranged in the base station 105.

The burette 120 may be a disposable article. An advantage of having the burette as a dispose article is that a step of washing and sterilising a complicated structure for use with another patient, or with the same patient at a later stage, is eliminated. The burette does not have to be manufactured in a rugged re-useable material capable of withstanding repeated washing and handling.

The capacitance electrodes 140 are preferably of a length reaching from a position corresponding to a bottom end of the burette and to a position corresponding to an upper end of the burette. The capacitance electrodes may end at a maximum filling level of the burette. Above this level self emptying takes place. The burette suitably empties into a conventional urinary collection bag attachable to the burette outlet 130, 160.

By inventive thinking and by experimentation, the inventor(s) have found that if the electrodes are arranged besides each other, the distance between them should be large in comparison with the thickness of the wall of the burette. Electrodes having a width of 5 to 20 mm should function well. However, the electrodes should be considerably less wide than the burette. This would reduce the risk of picking up disturbances or interference. Electrodes less wide than 5 mm may give a little bit weak signal, even if low signal level seems to appear first when the width becomes less than one mm.

The electrodes may be made wider as the burette widens upwards, such that a capacitance signal becomes linear with the volume, instead of with the height. For reasons of manufacturing technology, the burette may have taper angles. If the burette is manufactured from two halves, it is possible to have constant width inside.

The cavern 138, which also can be called "socket", of the base station 105 may be an open cavern, i.e., not completely surrounding the walls of the burette 120, enabling the burette including catheters connected to the inlet and the outlet to be placed in the cavern without the need to disconnect one or more of the catheters. The cavern is preferably provided with three walls; a back wall 136, a left side wall 139, and a right side wall 137, the cavern 138 is preferably open, or partly open, upwards and downwards to let inlet and catheter tubing pass from above, and to let outlet pass downwards. The cavern is preferably open at the front to enable visual inspection of the urine level in the burette 120. The left 139 and right 137 side walls may preferably be arranged slightly slanting to confer a narrowing cross section to the cavern in the downwards direction. Correspondingly, the burette may be given a slightly tapering shape to provide a snug and consistent fit of the burette in the cavern. The snug and consistent fit assures good measuring conditions for particularly the capacitance electrodes.

The burette may preferably have a measurement volume of between 10 and 30 milliliter, and even more preferred, a measurement volume of between 14 and 16 milliliter. These volumes have shown to be particularly advantageous as to the time the urine spends in the burette 120. It is an advantage to have fresh urine in the burette. However in a too small burette, capillary forces may interfere with the siphoning function, and/or the filling of the burette. The burette may be provided with a measuring scale for easy check of electronic measuring function.

The burette 120 may have a quadratic or oval cross section and be provided with two planar side walls to fit snugly toward the capacitance electrodes 140 of the cavern of the base station 105.

A front wall of the burette 120 may advantageously be made of a transparent polymer to allow for visual inspection of the siphon and the urine level inside. A visual measurement scale may be printed or cast at burette surface for visual measurement of urine level.

There may be arranged two conductance electrodes 148 on the inside of the burette to come into contact with the urine and which conductance electrodes 148 are connected to contact plates 150 arranged on the outside of the burette 120. The contact plates 150 arranged on the outside of the burette 120 may be arranged at a back wall 152 of the burette 120. Further, two connection contacts 145 may be arranged in a back wall 136 of the cavern to make contact to the contact plates 150 of the burette 120 to convey a conductance signal to the base station for signal processing and measurements.

The device may further be provided with means for combining capacitance and resistance/conductance measurements to improve volume measurements.

The outlet pipe 160 may be of a certain length and may be provided with a cross section area that is gradually increasing towards an outlet end.

Method of Processing the Measurement Signal(s)

The processing of signals is aimed to provide a urine production signal as a function of time. The base station may be provided with a display 125 for displaying the urine production as a function of time. A value representing the production the last hour may be displayed. A value representing the production the last 24 hours may be displayed. A value representing the current volume in the burette may be displayed. A value representing urine volume since last replacement of bag may be displayed.

The invention provides a method for signal processing of measured signals. The method comprises determination of at least one self-calibration point with the aid of a reference sensor. This enables the system to adjust to both a new measurement chamber and to identify and adjust for half emptying sequences. In the context of the present invention, a "self-calibration point" is a point on the sensor measurement curve that can be easily determined to correspond to a known value of what is ultimately to be measured, i.e., urine volume.

The method is devised to be capable to reveal whether signals are acceptable or not for further processing, and to alert thereof if a possible non-macroscopic degeneration of delicate surfaces seems to be in process. The method alerts the user to replace the disposable measurement chamber when a certain level of surface degeneration is detected to be present. The method allows replacement of the disposable measurement chamber during the course of treatment without losing information. The method is devised to detect when urine is flushing into the measurement chamber during the filling and emptying procedure and compensate calculations in order to prevent inaccurate readings of actual volume.

Self-Calibration

FIG. 3a shows a urine measuring device wherein a burette, i.e., a measurement chamber, is attached to a base unit having capacitive electrodes arranged on a flat surface. FIG. 2 shows the sensor electrode arrangement of FIG. 3a in greater detail. The sensor electrode arrangement comprises:
- a first electrode (E1) having a first portion (E1a) a) and a second portion (E1b);
- a second electrode (E2) having a first portion (E2a) and a second portion (E2b)

wherein the first portion and the second portion respectively, are arranged apart a first and a second distance respectively, in the direction of increasing urine level in the measurement chamber, and are also connected to each other by a conducting material.

The set of electrodes further comprises:
- a third electrode E3;
- a fourth electrode E4;

wherein the first and second electrodes are arranged with a length axis parallel to each other and with a length axis parallel to the direction of increasing urine level, and;

wherein the third electrode E3 is arranged having a major portion situated between the first portion E1a and the second portion E1b of the first electrode in the direction of increasing urine level, and;

wherein the fourth electrode E4 is arranged having a major portion between the first portion E1a and the second portion E1b of the first electrode in the direction of increasing urine level The first and the second electrodes are here called main electrodes. The third electrode E3 and the fourth electrode E4 are called reference electrodes. By placing a reference electrode in the middle of the main sensor in the disclosed sensor system the system may be able to calculate which sensor reading that corresponds to a urine level reaching to the lower boundary of the reference electrode One advantage of the a described system over a system with rectangular main electrodes having even width over their entire length is that the area the electrodes occupy can be made smaller and more compact. The solution is a linear adaptation to the sensor signal at the known volume. See further below.

Signal Processing

The urine measurement system comprises a signal processing unit connected to the capacitive sensors, i.e., the electrodes. As long as the surface of the measurement chamber is acceptable, i.e., without or with only small amounts of bio film and encrustation as described above, the signal will follow the liquid level. I.e., an increase in volume will correspond to an increase in signal. When the surface becomes degenerated to an unacceptable level the signal will not be able to follow the liquid level beyond the degenerated portion of the delicate surface. Time-constant would be a measure of the degenerated surface.

Figure 1G:
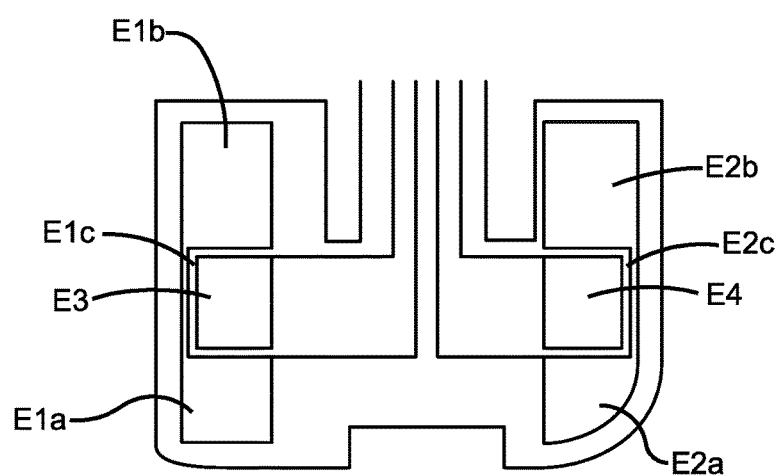
FIG. 1g shows a sensor electrode arrangement.
Figure 2A:
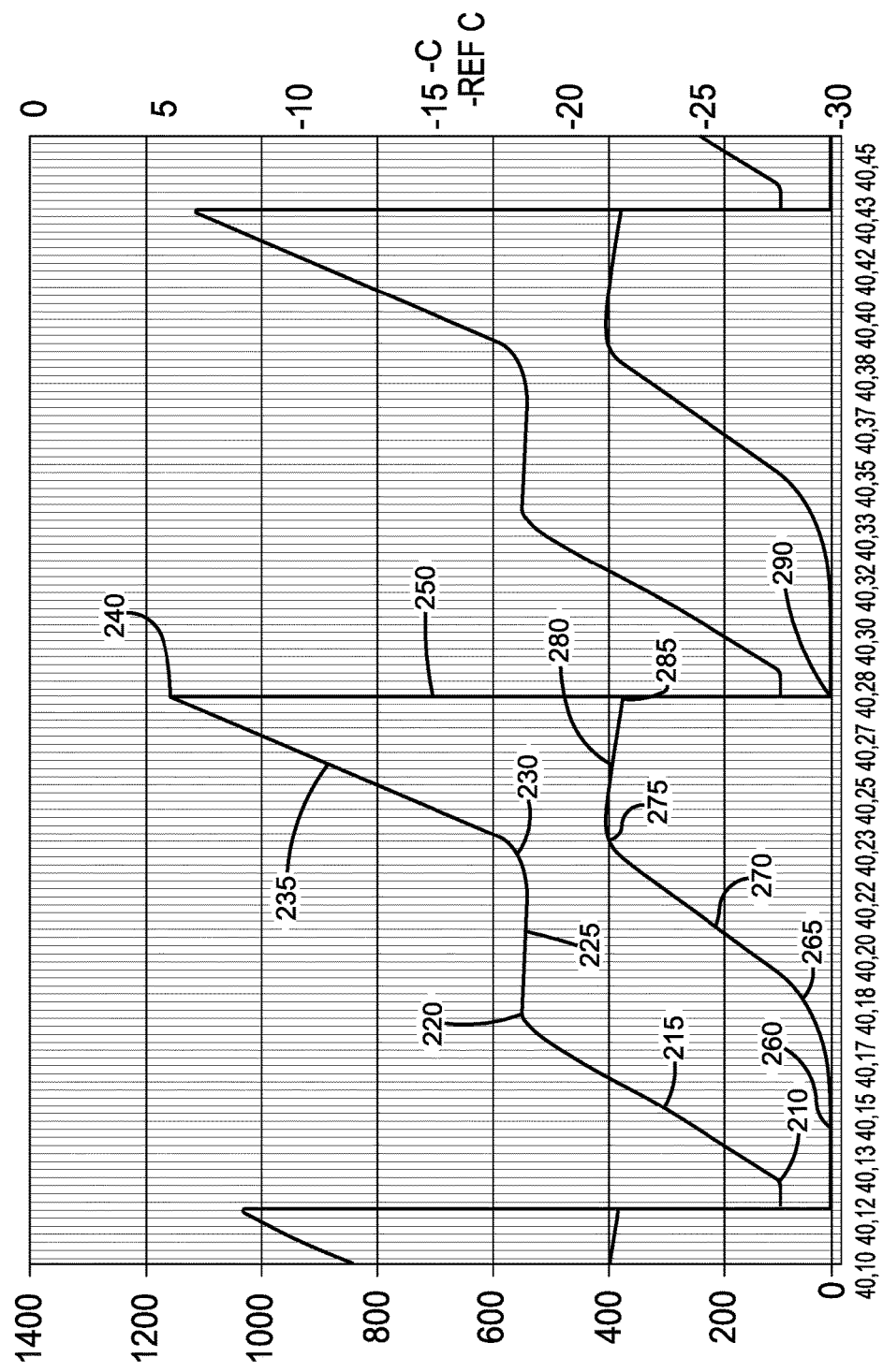
FIG. 2a shows an example diagram of how capacitance values of the sensor electrode arrangement of FIG. 1f may vary over time given a constant urine production under ideal conditions.

FIG. 2a shows an example diagram of how capacitance values of the sensor electrode arrangement of FIG. 1g may vary over time given a constant urine production under ideal conditions, i.e. measurements have just started and the measurement chamber is fresh. The capacitance Cm(t) measured between the main electrodes is represented by the curve with deflection points and legs denoted 210, 215, 220, 225, 230, 235, 240, 250, 290. The curve between points 210 and 290 represents one filling-emptying cycle. The capacitance Cr(t) measured between the reference electrodes is represented by the curve with deflection points and legs 260, 265, 270, 275, 280, 285, 290. The curve between beginning of leg 260 and point 290 represents one filling-emptying cycle for the reference electrodes.

Figure 2B:
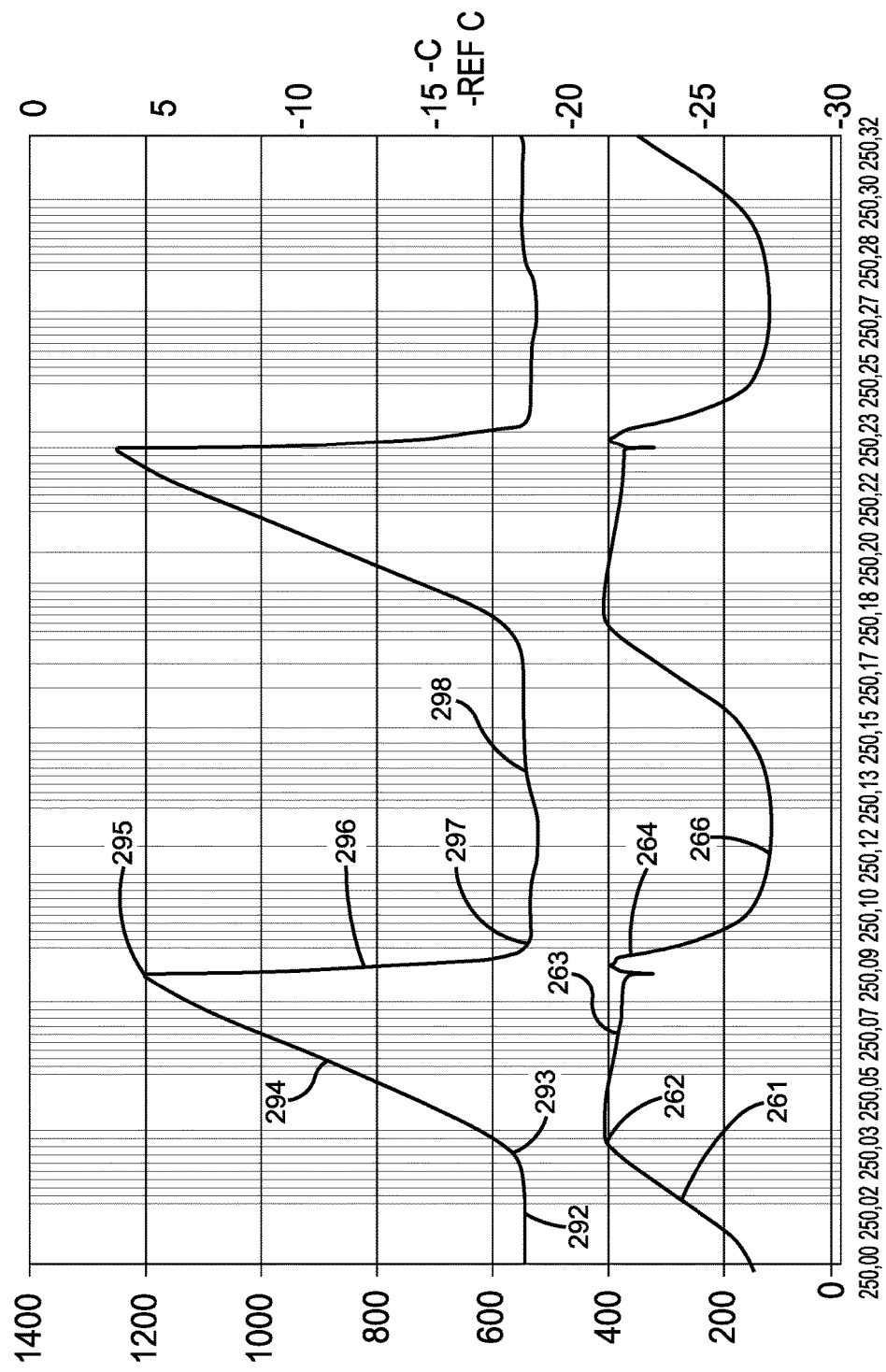
FIG. 2b shows an example diagram of how capacitance values of the sensor electrode arrangement of FIG. 1f may vary over time given a constant urine production under conditions of bad conditions involving formation of bio film and encrustation(s).

FIG. 2b shows an example diagram of how capacitance values of the sensor electrode arrangement of FIG. 1g may vary over time given a constant urine production under less favourable conditions involving formation of bio film and encrustation(s). The figure illustrates two emptying procedures 210 hours later than the signals of FIG. 2a. Here the sensors clearly begin to be saturated due to encrustation and/or bio film. It clearly takes long time for the sensor signal to drop after an emptying, and the sensor seems saturated up slightly above $c_{ref}$ sensor. In the FIG. 2b the capacitance Cm(t) measured between the main electrodes is represented by the curve with deflection points and legs denoted 292, 293, 294, 295, 296, 297, 298. In this figure, the capacitance Cr(t) measured between the reference electrodes is represented by the curve with deflection points and legs 261, 262, 263, 264, 266. As can be seen when comparing FIGS. 2a and 2b, it becomes harder for a human being to identify the phases of filling, i.e., when urine level is within the area of lower portion of main sensor, reference sensor, and higher portion of main sensor respectively.

Linear Function of Self Calibration

The invention provides a method for self calibration of the measured and displayed volume in the and/or passing the, measurement chamber. A function $$y=kx+m$$

is provided for calculating an estimated volume y in the measurement chamber on the basis of a variable x, representing a sensor value or a combined sensor value derived from multiple sensor values. The variable x increases as the volume of urine in the measurement chamber increases. The factor k is a proportionality factor that is determined by the self calibration method of the present invention, and provides subsequently a value of how much the volume y increases for each unit of increase of the variable x. The term m is an adjustment term that is also determined by the self calibration method of the present invention, and represents a correction term to ensure that the estimated volume y is zero when the measurement chamber is empty regardless of the measured sensor value or combined sensor values at that time. Thus, in short, y is urine volume, k is a proportionality factor, x is a sensor value, m is an adjustment term.

The self calibration method of the present invention determines k and m by solving the equation $$y=kx+m,$$

for y=0, and for y=y1 (a known volume).

The system becomes aware that the level corresponding to the known volume y1 is reached, when a further sensor signal indicates ditto, e.g., when an optic sensor arranged at that level indicates a change, or a further capacitive sensor appropriately arranged indicates a change.

The self calibration method of the present invention performs a renewed calculation of self calibration parameters, i.e., a new calculation of the factor k, and of the term m each time the measurement chamber is filled and/or emptied.

A urine measurement system may be provided with further sensors such that a further known volume y2 can be measured and used to increase accuracy of parameters k and m. y2 may be greater than y1

Method for Determining when the Surface Degeneration is Beyond Acceptable Levels.

When the surface becomes degenerated to an unacceptable level the signal will not be able to follow the liquid level beyond the degenerated portion of the delicate surface. The signal processing unit comprises means for determining a time-constant that constitutes a measure of the degenerated surface The system is also provided with means for alerting the user to change the disposable part, i.e., the measurement chamber.

The system may be provided with a baseline value memory. The baseline value is defined as the sensor reading corresponding to a newly emptied chamber. The inventor(s) has realised that the baseline value increases over time. By providing a baseline value memory and comparing the actual baseline value with the one at the first or second emptying in relation to sensor reading at full measurement chamber, the system is provided with alarm means to issue an alarm when the baseline value has reached a certain threshold. The threshold may be expressed as a percentage of the sensor value at full measurement chamber. The first measured baseline after a change of measurement chamber is called "initial baseline". In the context of the present invention, the phenomenon of increasing baseline value, is chosen to be named "baseline alteration". A function or unit that monitors or keeps track of baseline alteration may be called a "baseline level tracker".

The inventors have also devised a more general method for automatically, with the aid of a processor, determining surface degeneration of a surface that may not be a surface of a siphoning self-emptying measurement chamber but a general surface of a urine handling system, including e.g. a luminal surface of a catheter. The method comprises the following main steps:
a) repeatedly measuring one or more capacitive values of the surface, forming capacitive measurements;
b) storing all, or representative instants of the capacitive measurements;
c) deciding, based on particular changes of the stored capacitive measurements, that a significant surface degeneration has occurred.

In the step b) storing of representative instants of the capacitive measurements may be performed either regularly at defined time intervals, or controlled by a method selecting the lowest capacitive measurement during a "cycle". A cycle may be defined as either a filling and emptying cycle of a measurement chamber, or as a predetermined period of time. Such a predetermined period of time is preferable selected in the range of 30 to 60 minutes since urine produced by a patient's kidneys seem to be entering the bladder, and thus exiting the body via the catheter in runnels or tricklets, wherein there may be periods of non-discharging of urine. During these periods of inactivity it is best to make a measurement, since the capacitive value then is not likely to be disturbed by flowing urine, and at least one such non-discharging period should probably occur during such a predetermined period of time.

In the step c) the deciding is preferably performed by comparing the latest value with earlier values, such that a first lowest value measured during the first predetermined period, or a second lowest value measured during the second predetermined period, e.g. between 0-60, and 60-120 minutes respectively is compared to a latest lowest value measured during the latest period, i.e., the latest hour. If the latest lowest value is found to be significantly higher than the first or second lowest values, then it is decided that a significant surface degeneration has occurred. It may be advantageous to compare with an early value, but maybe not the first. The inventors have recognised that there may be a short time of very low capacitance value before the first urine wet the surfaces of urine system when it is first connected to the patient, hence the teaching to use the second time interval as described above. However, this initial effect of completely dry and unaffected surface, may also be handled by manual methods, e.g. by wetting the surface manually with a tricklet of urine from the patient.

Further, the inventors have also devised a device for performing the method of automatically, with the aid of a processor and a capacitive sensor, determining surface degeneration of a surface that may or may not be a surface of a siphoning self-emptying measurement chamber but a general surface of a urine handling system, including e.g. a luminal surface of a catheter. The device comprises a surface of a urine handling system, for example a luminal surface of a urine catheter or tube, which surface is exposed to urine;

a capacitive sensor, capable of repeatedly measuring one or more capacitance value of a structure involving the surface, forming a sequence of measurements;

a signal processing system, connected to the capacitive sensor, and capable of processing consecutive capacitive measurements, wherein the signal processing system is configured to decide, based on particular changes of the stored capacitive measurements, that a significant surface degeneration of the surface has occurred.

The deciding is preferably performed by comparing the latest value with earlier values, such that if the latest lowest value is found to be significantly higher than the first or second lowest values, then it is decided that a significant surface degeneration has occurred, as explained for the method above. If it is decided that a significant surface degeneration has occurred, the signal processing system may indicate this to a user by turning on an indicator, e.g. a lamp, a light emitting diode, a symbol on a screen or similar.

The arrangement of electrodes of the capacitive sensor is preferably such that a measured capacitance change due to surface degeneration forms a large portion of the total measured capacitance. Electrodes are arranged to allow for measurement of the capacitance and they may be arranged at the replaceable part, e.g. in a wall. More preferred is to not arrange the electrodes as part of the replaceable part, but at a support structure. This has the advantage of eliminating the need for electrical connections. The support structure are arranged to support the replaceable part on the non-luminal side of the replaceable part. The electrodes are preferably arranged on the outer side of a wall separating the urine from the outer environment.

Method for Management of Replacement of the Measurement Chamber During the Course of Treatment and Making the Signal Processing Unit Aware of the Same.

When the measurement chamber is removed from its position the capacitive signal(s) will instantly drop to zero. Or almost zero. Or in any case well below the latest established baseline value for an empty chamber. This sudden drop of signal serves as an indication to the measurement system that the disposable part is removed and will be replaced with a new part. The measurement system may hereby choose to stop measure and automatically start measurements when the disposable part is in its correct position. Insertion of a new chamber 120 is detected by a sudden increase in the capacitive signal(s). The signal processing unit is provided with a new-chamber-in-place detector for detecting when a new chamber 120 is in place.

Example 1

Please consider the following example of a method for robust determination of produced urine.

Definitions

Vth volume produced this hour

Vph volume produced previous hour; urinary output [in ml per hour]

Vsip(t) Volume in the siphoning measurement chamber as a function of time

Cm(t) Capacitance measured between main electrodes as a function of time

Cr(t) Capacitance measured between reference electrodes as a function of time

The capacitance signals are affected by a number of external factors, such as alignment and mounting of the sensor, alignment and positioning of the measurement chamber, offsets of the electronics etc. The invention provides means for adaptive self-calibration to make up for these external factors.

The concept of the invention may be more easily understood if considering an ideal case with constant urine production, i.e., with a constant inflow. In such a case, the relationship between the capacitive sensor signals and the volume looks like the ones depicted in FIGS. 4a, 4b, 4c, 4d. The capacitance curve 410 of the main sensor Cm is shown in FIG. 4b. The capacitance curve 415 of the reference sensor Cr is shown in FIG. 4c. The volume curve 420 corresponding to the sensor curves 410 and 415 is shown in FIG. 4d.

AUXILIARY DEFINITIONS

Va Fixed known volume corresponding to a urine level at the lower boundary of the reference sensor Vb Fixed known volume corresponding to a urine level at the upper boundary of the reference sensor Vth_bag The sum of emptying volumes during present hour Vtop The highest momentary volume during a filling-emptying cycle Vin_while_flush Inflowing volume during emptying Kflush A constant used to detect emptying. Based on a derivative of the volume.

Va and Vb are known, whereas Cm-ab(t), Cr-a(t) and Cr-b(t) are determined via measurements and are used as parameters for self calibration. In the following, "Cal" is used to denote the joint set of the self calibration parameters Cm-ab, Cr-a and Cr-b.

The momentary volume Vsip(t) is calculated by aligning the measurement signals with the aid of the self calibration parameters Cm-ab, Cr-a and Cr-b.

The volume at emptying is calculated as the highest volume during a filling-emptying cycle adjusted by adding an estimated volume that flows in during the emptying procedure.

The current hour volume Vth-bag is calculated as the sum of the volumes of earlier emptying procedures and the momentary one.

Figure 4E:
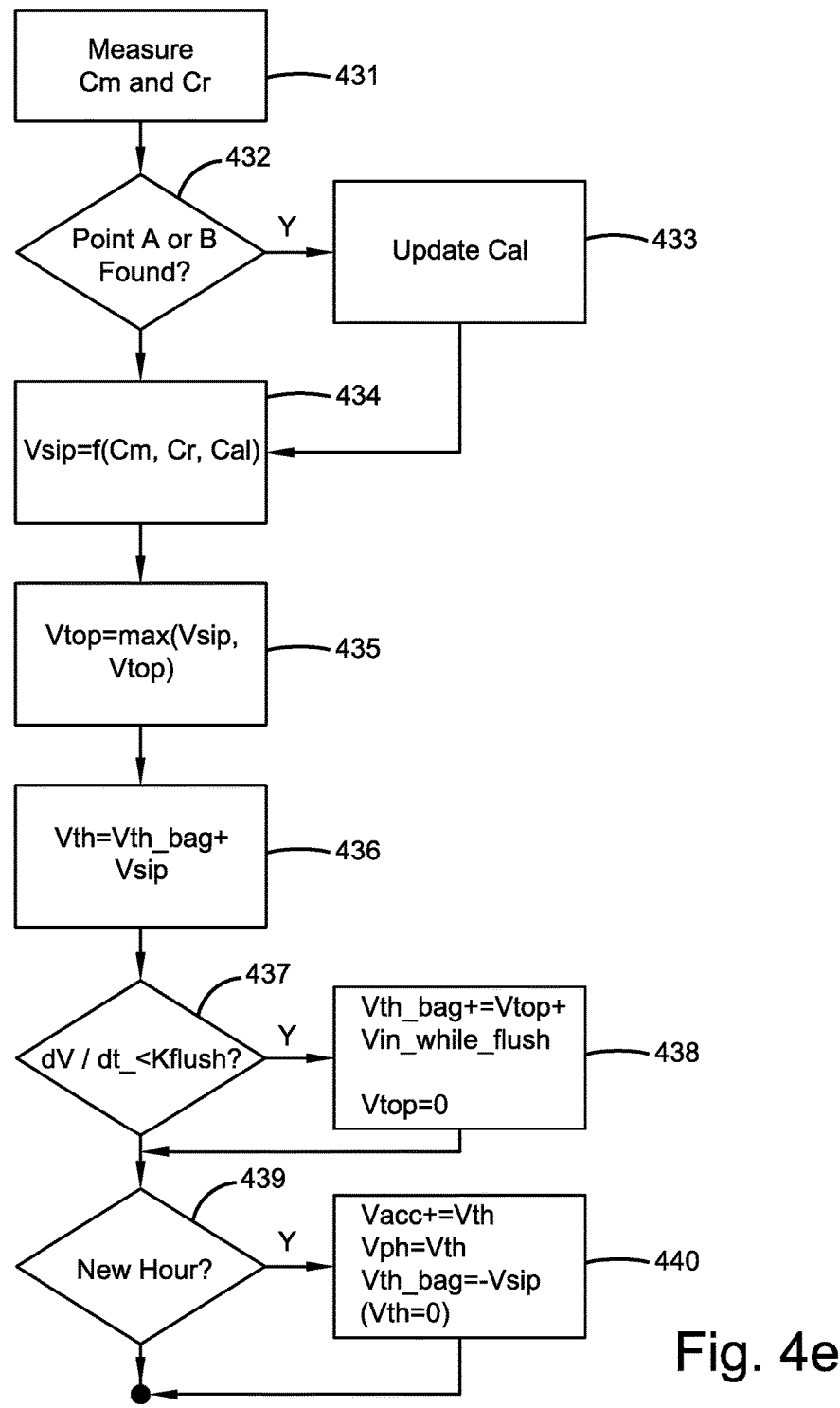
FIG. 4e shows a flowchart of a method for determining of urine production including self calibration.

FIG. 4e shows a flowchart of a method for determining of urine production including self calibration. The method includes the steps of:

Measuring Cm and Cr;

Deciding if point A or point B is found, and if so update Cal;

Setting Vsip to a function of Cm, Cr and Cal;

Setting Vtop to maximum of Vsip and former Vtop;

Setting Vth to Vth_bag+Vsip;

Deciding if derivative dVsip/dt is less than flush constant Kflush, and if so setting Vth_bag to Vtop+Vin_while_flush and Vtop subsequently to 0;

Deciding if a new hour has started, and if so setting Vacc to sum of Vacc and Vth, setting Vph to Vth, setting Vth_bag to minus Vsip–Setting Vth to zero Example 2

Referring now to FIG. 4f, below is found a descriptive list of actions and steps of a urine measurement device in practical use.
1. The measuring unit is installed into the base unit and the signal has established a baseline where signal starts.
2. The unit receives an inflow of liquid and hence signal is increasing at a certain angle against upwards
3. The liquid level reaches a first self calibration point at an estimated volume of 5 ml
4. The liquid level reaches a second self calibration point at an estimated volume of 10 ml
5. The liquid continues to fill the unit up to maximum level at an estimated volume of 15 ml
6. The self emptying chamber empties automatically and the signal drops rapidly just slightly above the initial baseline
7. When surface becomes degenerated due to aggressive properties of said liquid the baseline will become higher
8. When unit is filled and then emptied the signal will rapidly drop, but only to the altered baseline
9. When baseline alteration becomes too high (40% deviation from starting point for instance) and with reference to accuracy, performance and patient safety aspects, the system will indicate to the user that the unit shall be replaced with a new unit
10. When the unit is removed the signal will rapidly drop to the baseline of origin
11. (Back to 2-10)
12. A rapid flush of liquid increases throughput of said liquid and the signal changes its curve to become steeper during inflow and more extended during outflow. The new signal will be compensated due the change in volume by calculation of the angle of inflow curve and add a constant to the expected volume and hence none, or only limited volume will be lost during the measure of said liquid Example 3

Figure 5A:
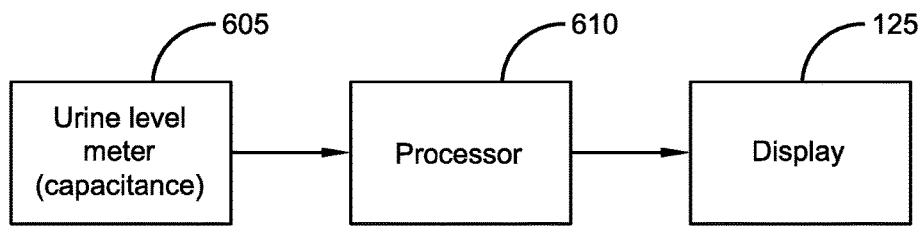
FIGS. 5a, 5b, and 5c shows possible general block diagrams of measurement systems.
Figure 5B:
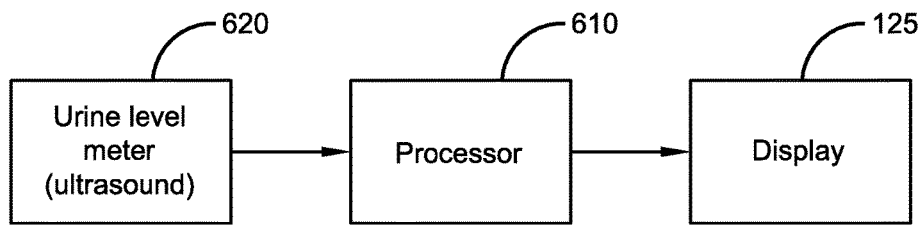
Figure 5C:
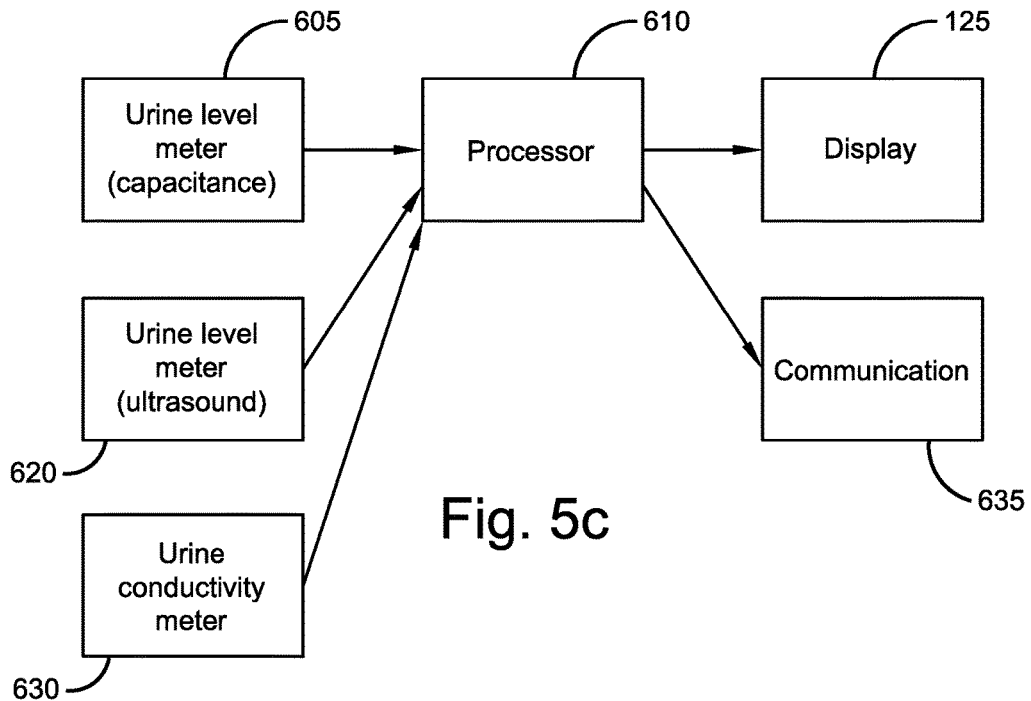
Figure 5D:
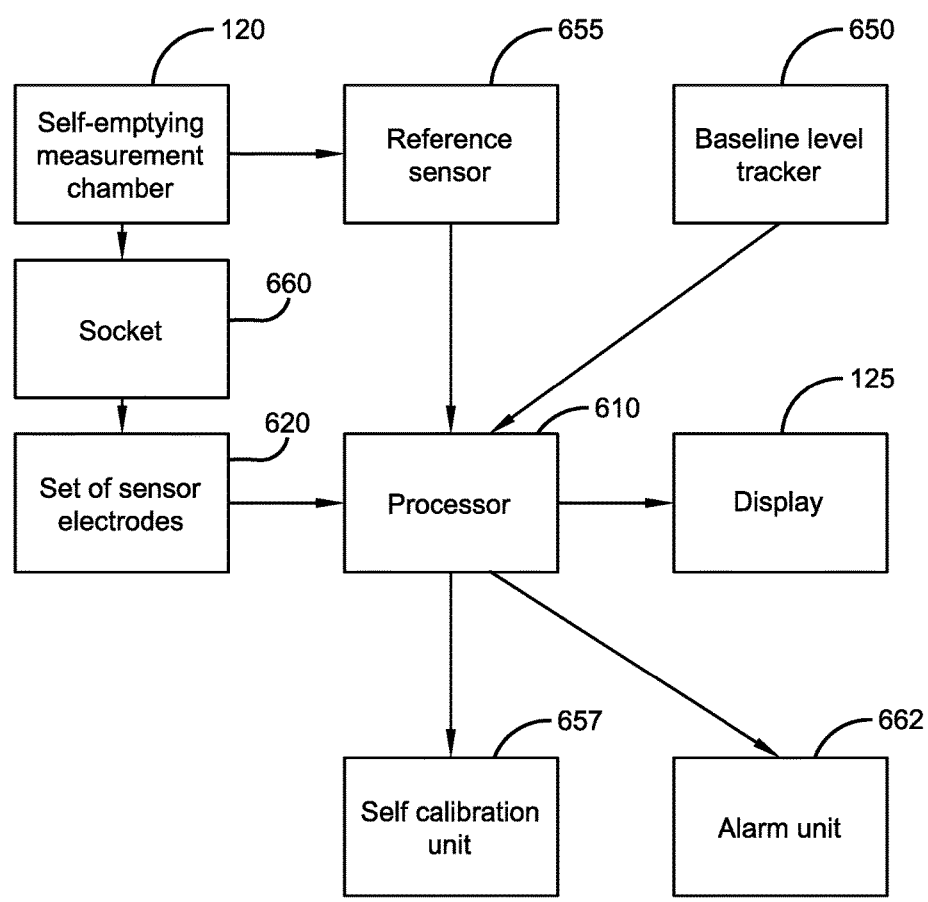
FIG. 5d shows a block diagram of a measurement system with a baseline tracker and a self calibration unit.
Figure 6:
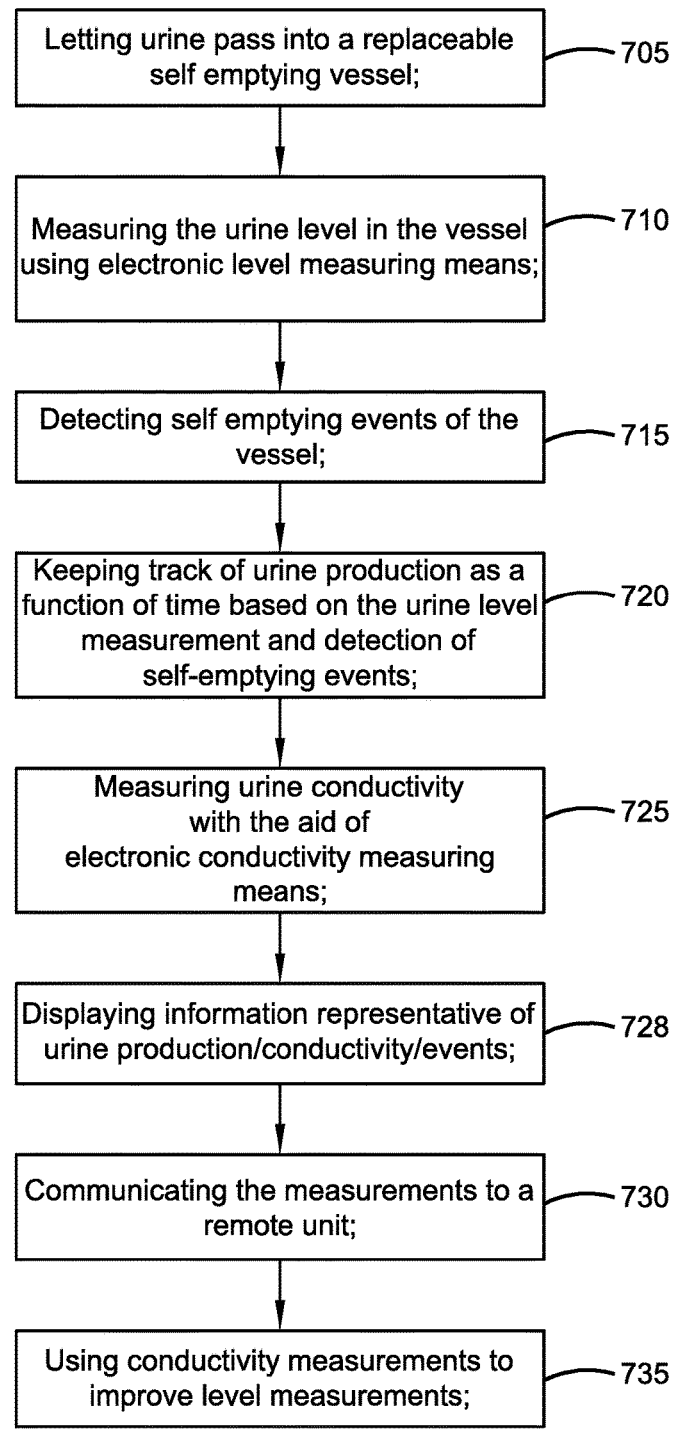
FIG. 6 shows a flow chart of a method for precise measuring of urine production of a patient.
Figure 7:
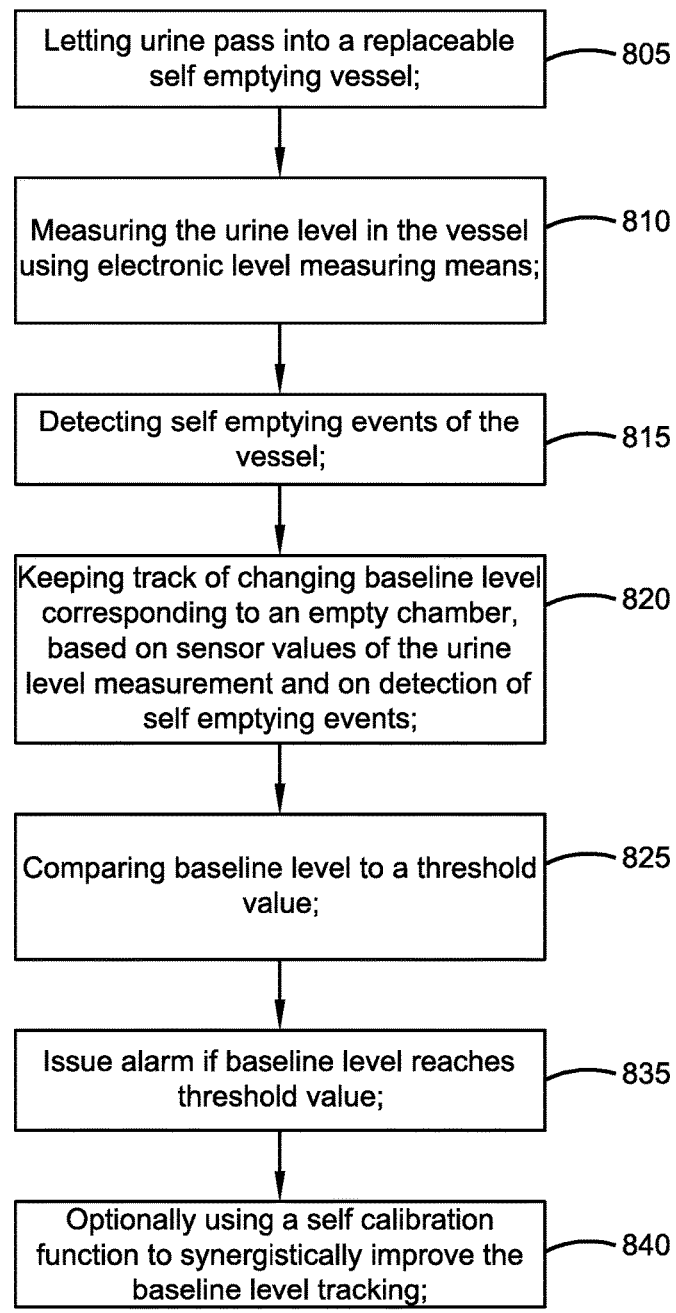
FIG. 7 shows a flowchart of a method for detecting measurement chamber degradation using a baseline tracker.
Figure 8:
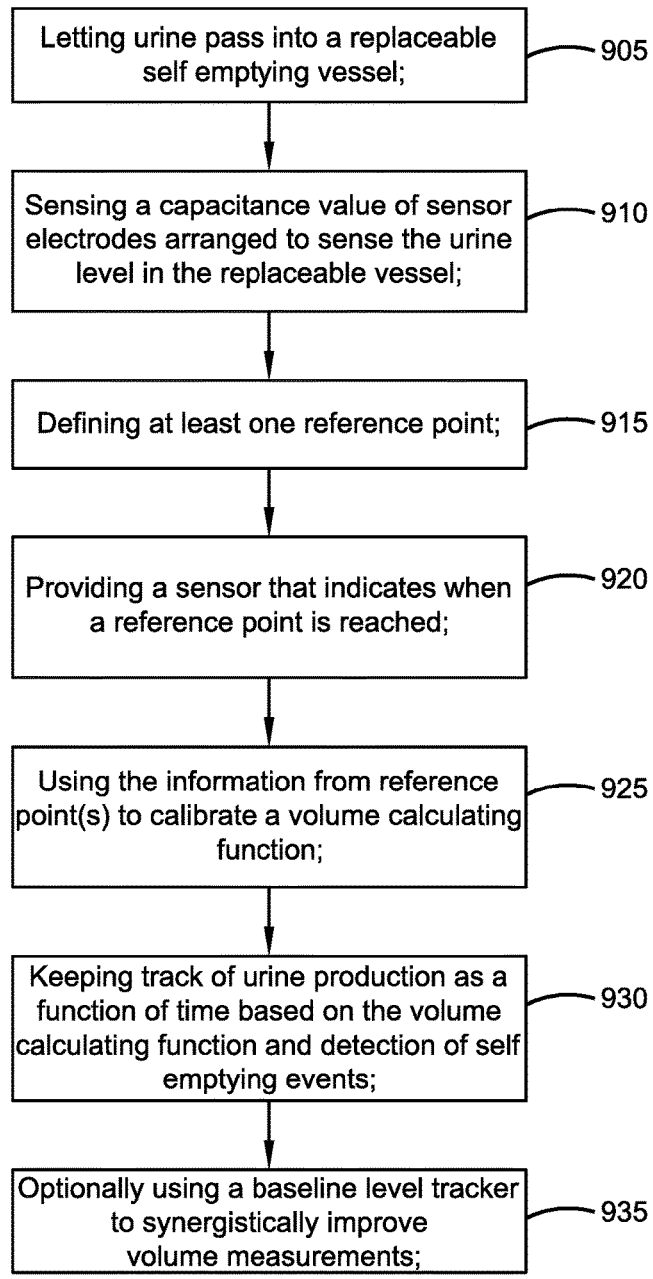
FIG. 8 shows a flowchart of a volume calculating method including self calibration steps.

Referring now to FIGS. 5d and 7 a method for baseline level tracking and detection of a compromised replaceable self emptying chamber is described.

The urine measuring device comprise:
a replaceable measurement chamber (120) to which urine from a patient is conveyed via a catheter to fill the measurement chamber,
a set of electrodes (620), comprising at least two electrodes, connected to a processor, and arranged to sense the changing capacitance corresponding to changing levels of urine in the replaceable measurement chamber,
emptying means to empty the measurement chamber when full,
a level sensor (655) for indication when urine level has reached a known position of the measurement chamber;
The method comprises the following steps:
Measuring (810) and/or deriving a sensed capacitance value (x, Cm(t)) corresponding to a capacitance between first two electrodes of the set of electrodes in turn corresponding to a urine level
Determining (820) an original baseline level equal to a sensed capacitance value corresponding to an empty measurement chamber;
Detecting (815) emptying events of the measurement chamber;
Measuring the capacitance corresponding to finished emptying events to measure new baseline level
Keeping track (820) of changing baseline level as multiple emptying events ensue;
Further, a self calibrating function, e.g. of the type described in this document, may be used to synergistically improve the baseline level tracking.

Example 4

There is provided a device for determining surface degeneration of a surface of a urine handling system, the device comprises
a first surface of a urine handling system, which first surface is exposed to urine;
a capacitive sensor, capable of repeatedly measuring one or more capacitance values of a structure involving the first surface, forming a sequence of measurements;
a signal processing system, connected to the capacitive sensor, and capable of processing consecutive capacitive measurements,
wherein the signal processing system is configured to decide, by deciding, based on changes of the stored capacitive measurements, that a significant surface degeneration of the first surface has occurred.
The deciding is preferably performed by comparing the latest value with earlier values, such that a first lowest value measured during a first predetermined period, or a second lowest value measured during a second predetermined period, is compared to a latest lowest value measured during a latest period, if the latest lowest value is found to be higher by a predetermined amount than the first alternatively the second, lowest values, then it is decided that a significant surface degeneration of the first surface has occurred.
The first surface is a surface of a luminal side of a replaceable part of the urine handling system, and the luminal side is arranged to come into contact with the urine, and the replaceable part has a proximity outer side, not intended to come into contact with urine but being in close proximity to the first surface of the luminal side, and wherein electrodes to be used for the capacitive measurements are arranged to fit close to the proximity outer side of the replaceable part.

The proximity outer side is preferably a surface directly opposing the first surface, but on the other side of a separating wall.
The separating wall is preferably a wall of a measurement chamber, or a tube, or a catheter.

Example 5

There is also provided a method for automatically, with the aid of a processor, determining a surface degeneration of a first surface of a urine handling system, the first surface being intended to come into contact with urine, the method comprises the following main steps:
a) repeatedly measuring one or more capacitive values of the first surface, forming capacitive measurements;
b) storing all, or representative instants of the capacitive measurements;
c) deciding, based on changes of the stored capacitive measurements, that a significant surface degeneration of the first surface has occurred.
The deciding is performed by comparing the latest value with earlier values, such that a first lowest value measured during a first predetermined period, or a second lowest value measured during a second predetermined period, is compared to a latest lowest value measured during a latest period, if the latest lowest value is found to be higher by a predetermined amount than the first alternatively the second, lowest values, then it is decided that a significant surface degeneration of the first surface has occurred.
The first surface is a surface of a replaceable part of the urine handling system, and the replaceable part has a luminal side coming into contact with urine, and a proximity outer side, not intended to come into contact with urine but in close proximity to the luminal side, and wherein electrodes to be used for the capacitive measurements are arranged to fit close to the proximity outer side of the replaceable part.
The proximity outer side is preferably a surface directly opposing the first surface, but on the other side of a separating wall.
The separating wall is preferably a wall of a measurement chamber, or a tube, or a catheter.

Descriptive Statements

Directly below are a number of descriptive statements organized as paragraphs numbered 1, 2 etc corresponding to the claims of the priority document. PCT claims will follow under the heading "CLAIMS"

1. A urine measurement device for measuring the production of urine of a patient wearing a urine catheter, wherein the device comprises a self-emptying measurement chamber (120) to which urine from the patient is conveyed via the catheter, the device is also provided with a set of electrodes (620) arranged to sense a changing capacitance (Cm(t)) corresponding to changing levels of urine in the self-emptying measurement chamber (120), wherein the set of electrodes comprises:
a first electrode (140, 310, 652)
a second electrode (320, 654)
between which the changing capacitance (x, Cm(t)) is measured, and wherein the device further comprises a socket (350, 136, 137, 138, 139, 660) for the self emptying measurement chamber (120), and wherein the self emptying measurement chamber (120) is replaceable and wherein the first and second electrodes (140, 310, 652, 320, 654) to sense the changing capacitance corresponding to changing levels of urine in the measurement chamber (120) are arranged at the socket wall (137, 139, 330) to face the measurement chamber (120), the device further comprises a data processing unit (610) connected to the electrodes (140, 310, 652, 320, 654) to keep track of produced urine volume and a baseline level tracker (650) arranged to determine and keep track of a varying baseline level, i.e., a capacitance value corresponding to an empty self-emptying measurement chamber, based on the changing capacitance, as multiple self-emptyings of the self-emptying measurement chamber ensue.

2. A urine measurement device for measuring the production of urine of a patient wearing a urine catheter, wherein the device comprises a self-emptying measurement chamber (120) to which urine from the patient is conveyed via the catheter, the device is also provided with a set of electrodes (620) arranged to sense a changing capacitance (Cm(t)) corresponding to changing levels of urine in the self-emptying measurement chamber (120), wherein the set of electrodes comprises:
a first electrode (140, 310, 652)
a second electrode (320, 654)
between which the changing capacitance (x, Cm(t)) is measured, and wherein the device further comprises a socket (660, 350, 136, 137, 138, 139) for the self emptying measurement chamber (120), and wherein the self emptying measurement chamber is replaceable and wherein the first and second electrodes to sense the changing capacitance corresponding to changing levels of urine in the measurement chamber are arranged at the socket wall to face the measurement chamber, and wherein the urine measurement device further comprises a reference sensor (655) arranged to detect and determine a first point in time when the urine level in the measurement chamber reaches a known predetermined level corresponding to a known volume, the device further comprises a data processing unit (610) connected to the electrodes (140, 310, 652, 320, 654) and arranged to keep track of produced urine volume, and a self calibration unit (657) arranged to determine and keep track of one or more self-calibration parameters, i.e., parameters that may be used to improve estimations of urine volume calculated from a measured capacitance value, based on the determined first point in time, the predetermined known volume, and the changing capacitance, as multiple self-emptyings of the self-emptying measurement chamber ensue.

3. The device according to paragraph 2 further comprising a baseline level tracker (650) to determine and keep track of a varying baseline level (451, 452, 453), i.e., a capacitance value corresponding to an empty self-emptying measurement chamber (120), based on the determined first point in time, the known volume, and the changing capacitance, as multiple self-emptyings of the self-emptying measurement chamber ensue.

4. The device according to paragraph 1 or 3, further comprising an alarm unit (662) capable of issuing an alarm when the baseline level reaches a predetermined threshold value.

5. The device according to any of the preceding paragraphs wherein the determinations of baseline level and/or self-calibration parameters are also based on the detection of start of self emptying events i.e., abrupt plummet of measured capacitance value 6. The device according to any of the preceding paragraphs wherein the determinations of baseline level and/or self-calibration parameters are also, or alternatively based on the detection of endpoint (462, 463) of self emptying events i.e., abrupt ceasing of plummeting measured capacitance value.

7. A urine measurement device for measuring the production of urine of a patient wearing a urine catheter, wherein the device comprises a measurement chamber to which urine from the patient is conveyed via the catheter, the device is also provided with a set of electrodes arranged to sense the changing capacitance corresponding to changing levels of urine in the measurement chamber, wherein the set of electrodes comprises:
a first electrode (E1) having a first portion (E1a) and a second portion (E1b);
a second electrode (E2) having a first portion (E2a) and a second portion (E2b)
wherein the first portion and the second portion respectively, are arranged apart a first and a second distance respectively, in the direction of increasing urine level in the measurement chamber, and are also connected to each other by a conducting material, the set of electrodes further comprises
a third electrode (E3);
a fourth electrode (E4);
wherein the first and second electrodes are arranged parallel to each other and with a length axis parallel to the direction of increasing urine level, and;
wherein the third electrode (E3) is arranged having a major portion between the first portion (E1a) and the second portion (E1b) of the first electrode in the direction of increasing urine level, and;
wherein the fourth electrode (E4) is arranged having a major portion between the first portion (E1a) and the second portion (E1b) of the first electrode in the direction of increasing urine level, and;
wherein a processing unit (610) is connected to the first, second, third, and fourth electrodes (E1, E2, E3, E4) and arranged to interpret changes in capacitance levels between the electrodes as corresponding to different levels of urine, and also corresponding to different physiochemical conditions inside the measurement chamber.

8. The urine measurement device according to paragraph 1 wherein the measurement chamber is of a self-emptying siphoning type.

9. The urine measurement device according to paragraph 2 wherein the measurement chamber is easy replaceable in a recess or docking site of the urine measurement device, and the electrodes are arranged at the walls of the recess or docking site such that they touch snugly towards a measurement chamber placed in the recess or docking site.

10. A method for detecting a compromised measurement chamber during measurement of urine production using a urine measuring device comprising:
a replaceable measurement chamber to which urine from a patient is conveyed via a catheter to fill the measurement chamber,
a set of electrodes, comprising at least two electrodes, connected to a processor, and arranged to sense the changing capacitance corresponding to changing levels of urine in the replaceable measurement chamber,
emptying means to empty the measurement chamber when full,
a level sensor for indication when urine level has reached a known position of the measurement chamber;
the method comprising the following steps:

Measuring and/or deriving a sensed capacitance value (x, Cm(t)) corresponding to a capacitance between first two electrodes of the set of electrodes Determining an original baseline level equal to a sensed capacitance value corresponding to an empty measurement chamber;

Detecting emptying events of the measurement chamber;

Measuring the capacitance corresponding to finished emptying events to measure new baseline level Keeping track of changing baseline level as multiple emptying events ensue;

11. The method of paragraph 10 further comprising the step:

issuing an alarm when the baseline level has reached a predetermined threshold.

12. The method according to paragraph 10 or 11 wherein the detecting of emptying events is based on detection of endpoint of self emptying events i.e., abrupt ceasing of a plummeting measured capacitance value.

13. A method for measuring urine production using a urine measuring device comprising a measurement chamber to which urine from the patient is conveyed via a catheter to fill the measurement chamber, a set of electrodes, comprising at least two electrodes, connected to a processor, and arranged to sense the changing capacitance corresponding to changing levels of urine in the measurement chamber, emptying means to empty the measurement chamber when full, a level sensor for indication when urine level has reached a know position; the method comprising the following steps:

A—Measuring and/or deriving a first capacitance value (x, Cm(t)) corresponding to a capacitance between first two electrodes of the set of electrodes B—Defining a reference points corresponding to a known urine volume in the measurement chamber;

C—Providing a sensor that indicates when the known urine volume is reached

D—Using the information gathered in the above steps to effectively calibrate a volume calculating function, during each filling-emptying cycle, E—Calculating an estimated urine volume using the calibrated volume calculating function.

14. The method according to paragraph 13 wherein a volume estimation function is provided of the type $y=kx+m$ wherein y is the estimated volume, k is a first calibration parameter, x is a measured and/or derived capacitance value, and m is a second calibration parameter, and wherein the volume estimation function is used to estimate the urine volume production, and wherein the calibration parameters k and m are determined by solving, with the aid of the processor, the equation y=kx+m for at least two known values of y, during the normal operation of the urine measurement system of the method.

15. A method for measuring urine production using a urine measuring device comprising a measurement chamber to which urine from the patient is conveyed via a catheter to fill the measurement chamber, the device also being provided with a set of electrodes connected to a signal processing unit, and arranged to sense the changing capacitance corresponding to changing levels of urine in the measurement chamber, the device also being provided with emptying means to empty the measurement chamber when full, the method comprising the following steps:

a—Measuring a main capacitance Cm(t) between first two electrodes of the set of electrodes b—Measuring a reference capacitance Cr(t) between second two electrodes of the set of electrodes;

c—Defining reference points corresponding to actual physical boundaries of the first and/or second electrodes (which the urine level surface will pass by during filling and emptying;

d—Using the curves of Cm(t) and Cr(t) to identify the capacitance(s) corresponding to actual physical boundaries of the first and/or second electrodes;

e—Using the information gathered in the above steps to effectively calibrating the sensors during each filling-emptying cycle, and to display as accurate volume readings as possible.

16. The method according to paragraph 13 or 15 further comprising the following step(s):

Determining the measurement chamber current volume Vsip to be a function of main capacitance Cm(t), reference capacitance Cr(t) and calibration parameters corresponding to capacitances measured when urine level is equal to an upper or lower end of an electrode 17. The method according to paragraph 13 or 14 further comprising the steps of:

Determining a value of the highest momentary volume Vtop during a filling-emptying cycle to maximum of the volume in the measurement chamber Vsip and former highest momentary volume Vtop;

Determining the volume produced this hour, Vth, to be the sum of present sum of emptying volumes during present hour, Vth_bag, and the volume of the urine in the measurement chamber, Vsip;

Deciding if derivative dV/dt is less than flush constant Kflush, and if so setting the sum of emptying volumes during present hour Vth_bag to the sum of highest momentary volume Vtop and inflowing volume during emptying Vin_while_flush and setting highest momentary volume Vtop subsequently to 0;

18. The method according to paragraph 15, 16 or 17 further comprising the step(s) of:

Deciding if a new hour has started, and if so setting total accumulated urine volume Vacc to the sum of total accumulated urine volume Vacc and volume produced this hour Vth, and setting volume produced previous hour Vph to volume produced this hour Vth, and setting the sum of emptying volumes during present hour Vth_bag to minus the volume in the measurement chamber Vsip Setting volume produced this hour, Vth to zero

The invention claimed is:

1. A device for determining surface degeneration of a surface of a urine handling system, the device comprising:

a first surface of a siphoning self-emptying measurement chamber that is exposed to urine;

a capacitive sensor capable of measuring capacitance values of a structure involving the first surface; and a signal processing system connected to the capacitive sensor and capable of processing capacitive measurements received therefrom, wherein the signal processing system is configured to determine that significant surface degeneration of the first surface has occurred by:

determining a first baseline value based on a first measured capacitance value from the capacitive sensor corresponding to the siphoning self-emptying measurement chamber being newly emptied by a first emptying procedure, determining a second baseline value based on a second measured capacitance value from the capacitive sensor corresponding to the siphoning self-emptying measurement chamber being newly emptied by a second emptying procedure after the first emptying procedure, and comparing the second baseline value to the first baseline value to obtain a baseline alteration value, wherein the signal processing system determines that significant surface degeneration of the first surface has occurred when the baseline alteration value is larger than a threshold.

2. The device according to claim 1, wherein the first surface is a surface of a luminal side of a replaceable part of the urine handling system, and wherein the luminal side is arranged to come into contact with the urine, and wherein the replaceable part has a proximity outer side, not intended to come into contact with urine but being in close proximity to the first surface of the luminal side, and wherein electrodes to be used for the capacitive measurements are arranged to fit close to the proximity outer side of the replaceable part.

3. The device according to claim 2, wherein the proximity outer side is a surface directly opposing the first surface, but on the other side of a separating wall.

4. The device according to claim 3, wherein the separating wall is the wall of a measurement chamber, or a tube, or a catheter.

5. The device according to claim 1, wherein the first emptying procedure corresponds to an emptying procedure after an initial emptying procedure of the siphoning self-emptying measurement chamber.

6. The device according to claim 1, wherein the threshold is a percentage of a full measured capacitance value of the structure involving the first surface corresponding to the siphoning self-emptying measurement chamber being in a full condition.

7. The device according to claim 1, wherein the first measured capacitance value from the capacitive sensor corresponding to the siphoning self-emptying measurement chamber being newly emptied by the first emptying procedure corresponds to a first lowest measured capacitance value during a cycle of the siphoning self-emptying measurement chamber.

8. The device according to claim 4, wherein the cycle corresponds to a predetermined period of time.

9. The device according to claim 4, wherein the cycle corresponds to a filling and emptying cycle of the siphoning self-emptying measurement chamber.

10. The device according to claim 4, wherein the second measured capacitance value from the capacitive sensor corresponding to the siphoning self-emptying measurement chamber being newly emptied by the second emptying procedure corresponds to a second lowest measured capacitance value during the cycle of the siphoning self-emptying measurement chamber.

* * * * *